US006482230B1

(12) United States Patent
Chan et al.

(10) Patent No.: US 6,482,230 B1
(45) Date of Patent: Nov. 19, 2002

(54) LENS EPITHELIAL CELL GROWTH ASSAY FOR INTRAOCULAR LENS MATERIALS

(75) Inventors: Kwan Chan, Fort Worth, TX (US); John W. Sheets, Jr., Fort Worth, TX (US); Mutlu Karakelle, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 176 days.

(21) Appl. No.: 09/645,465

(22) Filed: Aug. 23, 2000

Related U.S. Application Data

(63) Continuation-in-part of application No. 09/283,589, filed on Apr. 1, 1999, now abandoned.
(60) Provisional application No. 60/081,890, filed on Apr. 15, 1998.

(51) Int. Cl.[7] .................................................. A61F 2/16
(52) U.S. Cl. ...................................... 623/6.61; 623/6.16
(58) Field of Search ............................. 623/6.61, 6.16, 623/912

(56) References Cited

U.S. PATENT DOCUMENTS

| | | | |
|---|---|---|---|
| 4,515,794 A | 5/1985 | Emery et al. | 514/249 |
| 4,725,276 A | 2/1988 | Bissonette et al. | 623/6 |
| 4,846,833 A | 7/1989 | Cumming | 623/6 |
| 4,918,165 A | 4/1990 | Soll et al. | 530/391 |
| 4,950,290 A | 8/1990 | Kamerling | 623/6 |
| 5,002,571 A | 3/1991 | O'Donnell, Jr. et al. | 623/6 |
| 5,078,740 A | 1/1992 | Walman | 623/36 |
| 5,290,892 A | 3/1994 | Namdaran et al. | 526/259 |
| 5,331,073 A | 7/1994 | Weinschenk, III et al. | 526/264 |
| 5,359,021 A | 10/1994 | Weinschenk, III et al. | 526/264 |

(List continued on next page.)

FOREIGN PATENT DOCUMENTS

| | | |
|---|---|---|
| EP | 0 559 820 B1 | 9/1993 |
| EP | 0 904 747 A2 | 3/1999 |
| EP | 0 916 320 A2 | 5/1999 |
| WO | WO 98/15238 | 4/1988 |
| WO | WO 94/11764 | 5/1994 |
| WO | WO 96/34629 | 11/1996 |
| WO | WO 99/62435 | 12/1999 |

OTHER PUBLICATIONS

Kurosaka et al., "Inhibition of Lens Epithelial Cell Migration by an Acrylic Intraocular Lens in vitro," *Ophthalmic Research*, vol. 34, pp. 29–37 (2002).
Boulton et al., "Adhesion of IOLs to the Posterior Capsule," *British Journal of Ophthalmology*, vol. 82(5); p. 468 (1998).
Cunanan et al., "An In Vitro Test Method to Study Posterior Capsular Opacification," *Investigative Ophthalmology & Visual Science*, vol. 38(4), p. S178 (1997).
Gabriel et al., "In Vitro Adherence of *Pseudomonas aeruginosa* to Four Intraocular Lenses," *J. Cataract Refractive Surg*, vol. 24, pp. 124–129 (1998).
Hollick et al., "Lens Epithelial Cells Regression on the Posterior Capsule: A 2 Year Prospective, Randomised Trial With Three Different IOL Materials," *Investigative Ophthalmology & Visual Science*, vol. 38(4), p. S19 (1997).

(List continued on next page.)

*Primary Examiner*—Corrine McDermott
*Assistant Examiner*—Javier G. Blanco
(74) *Attorney, Agent, or Firm*—Patrick M. Ryan

(57) ABSTRACT

A method for determining the propensity of an intraocular lens material to prevent posterior capsule opacification is disclosed. The method involves contacting a sample of an IOL material having the shape of an IOL optic with collagen to form a contact area, incubating the sample in a liquid composition comprising lens epithelial cells, determining whether lens epithelial cells grow on the collagen in the contact area.

2 Claims, 1 Drawing Sheet

U.S. PATENT DOCUMENTS

| | | | | |
|---|---|---|---|---|
| 5,366,501 | A | 11/1994 | Langerman | 623/6 |
| 5,370,687 | A | 12/1994 | Poler | 623/6 |
| 5,375,611 | A | 12/1994 | Lindqvist et al. | 128/898 |
| 5,405,385 | A | 4/1995 | Heimke et al. | 623/6 |
| 5,549,670 | A | 8/1996 | Young et al. | 623/6 |
| 5,576,345 | A | 11/1996 | Mansson et al. | 514/449 |
| 5,593,438 | A | 1/1997 | Akhavi et al. | 623/6 |
| 5,693,094 | A | 12/1997 | Young et al. | 623/6 |
| 5,733,276 | A | 3/1998 | Belkin | 606/6 |
| 6,027,531 | A | 2/2000 | Tassignon | 623/6 |
| 6,186,148 | B1 * | 2/2001 | Okada | 128/898 |

OTHER PUBLICATIONS

Johnston et al., "In Vitro Protein Adsorption to 2 Intraocular Lens Materials," *J. Cataract & Refractive Surgery*, vol. 25, pp. 1109–1115 (1999).

Kanagawa et al., "Presence and distribution of fibronectin on the surface of implanted intraocular lenses in rabbits," *Graefe's Archive for Clinical & Exp. Ophthalmology*, vol. 228, pp. 398–400 (1990).

Linnola et al., "Acrylate Intraocular Lenses (IOLs) Hinder Posterior Migration of Epithelium; Activity Tested by Corneal Tissue Cultures," *ESCRS Abstracts*, p. 120 (1997).

Linnola et al., "Adhesion of soluble fibronectin, laminin, and collagen type IV to intraocular lens materials," *J. of Cataract & Refractive Surgery*, vol. 25 (11), pp. 1486–1491 (1999).

Linnola et al., "Intraocular lens bioactivity tested using rabbit corneal tissue cultures," *J. Cataract & Refractive Surgery*, vol. 25, pp. 1480–1485 (1999).

Linnola, "Sandwich Theory: Bioactivity–based Explanation for Posterior Capsule Opacification," *J. Cataract Refract. Surg.*, vol. 23, pp. 1539–1542 (1997).

Liu et al., "A Study of Human Lens Cell Growth In Vitro," *Investigative Oph. & Visual Science*, vol. 37(5), pp. 906–914 (1996).

Mandle, "Acrylic Lenses Cause Less Posterior Capsule Opacification than PMMA, Silicone IOLs," *Ocular Surgery News*, vol. 14(15) (1996).

Nagamoto et al., "Effect of Intraocular Lens Design on Migration of Lens Epithelial Cells Onto the Posterior Capsule," *J. Cataract Refract Surg.*, vol. 23, pp. 866–872 (1997).

Nagata et al., "Adhesiveness of AcrySof to a Collagen Film," *J. Cataract Refract. Surg.*, vol. 24, pp. 367–370 (1998).

Nagata et al., "Optic Sharp Edge or Convexity: Comparison of Effects of Posterior Capsular Opacification," *Jpn J. Ophthal.*, vol. 40, pp. 397–403 (1996).

Nishi et al., Inhibition of Migrating Lens Epithelial Cells By Blocking The Adhesion Molecule Integrin: A Preliminary Report, *J. Cataract Refract. Surg*, vol. 23 (1997).

Oshika et al., "Adhesion of Lens Capsule to Intraocular Lenses of Polymethylmethacrylate, Silicone and Acrylic Foldable Materials: An Experimental Study," *British Journal of Ophthalmology*, vol. 82, pp. 549–553 (1998).

Oshika et al., "Incision/Phacoemulsification," Symposium on Cataract, IOL and Refractive Surgery, Jun., 1996.

Oshika et al., "Two Year Clinical Study of a Soft Acrylic Intraocular Lens," *J. Cataract Refract. Surg.*, vol. 22, pp. 104–109 (1996).

Pande et al., "High–Resolution Digital Retroillumination Imaging of the Posterior Lens Capsule After Cataract Surgery," *J. Cataract Refract. Surg.*, vol. 23, pp. 1521–1527 (1997).

Pande et al., "Posterior Capsular Opacfication With PMMA, Silicone and Acrysof Intraocular Lenses: A Prospective Randomized Clinical Trial," *Investigative Ophthalmology & Visual Science*, vol. 36(4), p. S397 (1995).

Reich et al., "Intraocular–Lens–Endothelial Interface: Adhesive Force Measurements," *J. of Biomedical Materials Research*, vol. 18, pp. 737–744 (1984).

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Ursell et al., Anterior Capsule Stability in Eyes With Intraocular Lenses Made of Poly(methyl methacrylate), Silicone, and AcrySof, *J. Cataract Refractive Surg.*, vol. 23, pp. 1532–1538 (1997).

Ursell et al., "Relationship Between Intraocular Lens Biomaterials and Posterior Capsule Opacification," *J. Cataract Refractive Surg.* vol. 24, pp. 352–360 (1998).

Ursell et al., "The In Vivo Movement of Cells on the Surface of Intraocular Lenses in Humans Observed with Sequential Specular Photomicrography," *Investigative Ophthalmology & Visual Science*, vol. 36(4), S795 (1995).

Werner et al., "Endothelial Damage Caused by Uncoated and Fluorocarbon–Coated Poly(methyl methacrylate) Inraocular Lenses," *J. Cataract Refractive Surgery*, vol. 23, pp. 1013–1019 (1997).

Yang et al., "Membrane Formation and Cellular Response on the Surface of Lenses Implanted in Rabbit Eyes," *J. Cataract Refractive Surg.*, vol. 23, pp. 1265–1270 (1997).

* cited by examiner

LENS EPITHELIAL CELL GROWTH ASSAY FOR INTRAOCULAR LENS MATERIALS

This application is a continuation-in-part of U.S. Ser. No. 09/283,589, filed Apr. 1, 1999, now abandoned which claims priority from U.S. Provisional Patent Application, U.S. Ser. No. 60/081,890, filed Apr. 15, 1998.

FIELD OF THE INVENTION

This invention relates to intraocular lenses. In particular, the present invention relates to methods for determining whether intraocular lens materials have a propensity for preventing posterior capsule opacification.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, *Foldable Intraocular Lenses*, Ed. Martin et al., Slack Incorporated, Thorofare, N.J. (1993). Biocompatibility varies among different IOL materials within and among each category.

One measure of biocompatability for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15, p.23 (1996). See, also, Oshika, et al., "Two Year Clinical Study of a Soft Acrylic Intraocular Lens," J. Cataract. Refract. Surg., 22:104–109 (1996); and Ursell et al., "Relationship Between Intraocular Lens Biomaterials and Posterior Capsule Opacification," J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. Nos. 5,576, 345 (pharmaceutical agent=the cytotoxic agent taxol or an ophthalmically acceptable derivative); 4,515,794; and 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts." Yet another method involves the physical destruction or removal of lens epithelial cells. See, Saika et al., J. Cataract Refract. Surg., 23:1528–1531 (1997).

Another method of addressing PCO is the prophylactic laser therapy method disclosed in U.S. Pat. No. 5,733,276. According to this method, the lens capsule is irradiated with laser irradiation to destroy cells which remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment preventing compound onto the posterior surface of the lens capsule. The stable or permanent layer may be a polymer, such as polyethylene glycol, polysaccharides, polyethylenepropylene glycol, and polyvinyl alcohols.

SUMMARY OF THE INVENTION

The present invention relates to a method of determining the propensity of an intraocular lens ("IOL") material to prevent posterior capsule opacification ("PCO"). The method involves contacting a sample of the IOL material having the shape of an IOL optic with collagen material thereby defining a contact area, incubating the sample in a liquid composition comprising lens epithelial cells ("LECs"), and determining whether any LECs grow on the collagen surface in the contact area.

The present invention also relates to IOL materials having reduced risk of PCO. Without intending to be bound by any theory, it is believed that an IOL material that adheres strongly to collagen upon contacting collagen prevents or inhibits LEC growth in the area between the collagen and the IOL material.

DETAILED DESCRIPTION OF THE INVENTION

According to the present invention, the propensity of an IOL material to prevent PCO is determined. The present invention relates to a method of determining whether an IOL optic will prevent LECs from growing on the posterior lens capsule, wherein the IOL optic has a posterior side having a radius of curvature and the method comprises the steps of:

(a) obtaining a container having an interior bottom surface of about the same radius of curvature as the posterior side of the optic, wherein the interior bottom surface comprises a collagen surface;

(b) contacting the posterior side of the optic with the collagen surface to form a contact area, optionally under a weight;

(c) plating lens epithelial cells on the collagen surface in an area surrounding the optic;

(d) incubating the lens epithelial cells for a time otherwise sufficient to allow the lens epithelial cells to grow to the center of the contact area; and (e) determining whether and to what extent lens epithelial cells grew on the collagen surface in the contact area.

Figure 1:
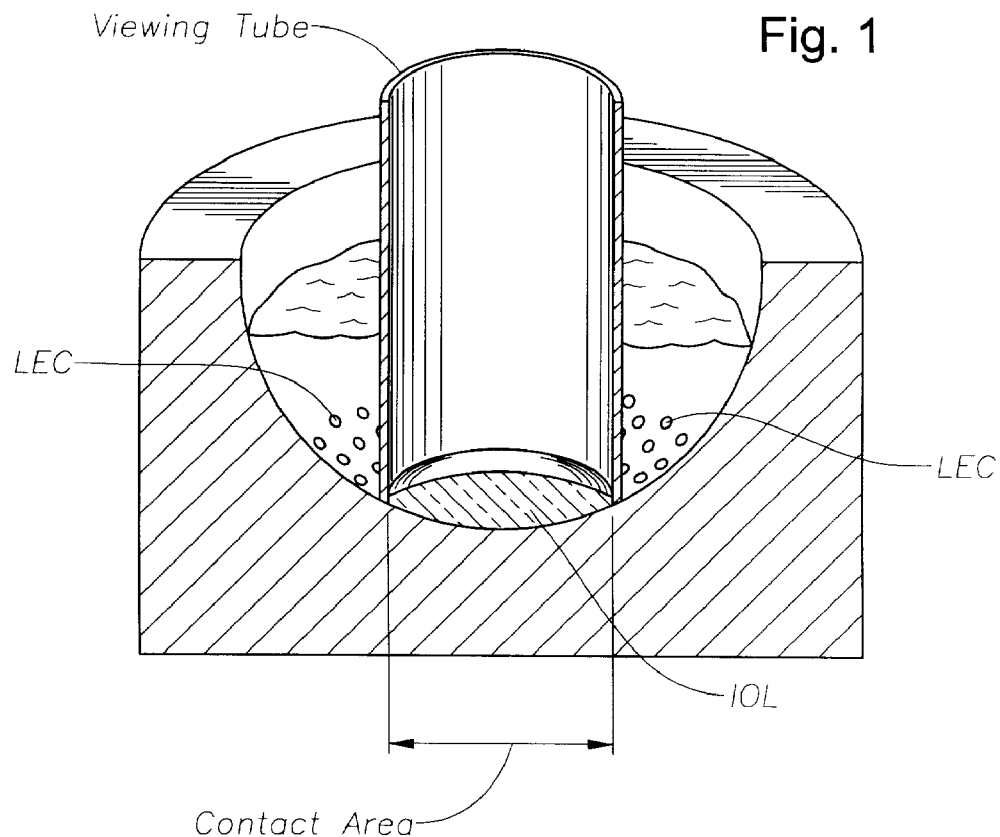
FIG. 1 shows an example of a test apparatus suitable for use in the assay of the present invention.

FIG. 1 is an illustration of a test apparatus for conducting the method of the present invention. The container has an interior bottom surface of about the same radius of curvature of the sample optic to be tested. The container can be plastic, for example, but its interior surface is coated with collagen.

Many types of collagen from different species are commercially available and are suitable for use in the present method. For example, human, rabbit and bovine collagen is available. Collagen of types I or IV are preferred. Collagen is available in sheet form (e.g., collagen I) or powder form (e.g., collagen IV). Collagen sheets can be applied as a coating over the container's interior surface. Dry powder collagen can be dissolved, typically with the help of a dilute weak acid, e.g., acetic acid, and deposited as a spin cast coating, for example.

The sample optic's posterior surface (or, if anterior and posterior surfaces are not defined for the sample optic, a surface simulating the radius of curvature and surface area of a posterior optic surface) is contacted with the collagen surface of the container to form a contact area. The sample optic is preferably held in contact with the collagen surface by means of a weight. The weight is preferably about 0.5–1.5 g and is preferably configured, for example as a viewing or transparent cylinder, to facilitate examination of the test apparatus using an inverted light microscope having phase contrast optics. A preferred weight is a transparent viewing cylinder of about 1 g.

The LECs are plated either directly or indirectly in the area surrounding the contact area. No LECs should be plated directly on the sample optic's anterior surface. This is easily prevented when a weight having the diameter of the sample optic is placed on the anterior surface of the sample optic prior to plating. The LECs can be directly plated by applying a suspension of LECs to the container. Alternatively, the LECs can be indirectly plated by placing pieces of lens capsule tissue on the collagen surface around the contact area (i.e., by "seeding" the LECs). Sources of LECs include immortalized cell lines, LECs grown from human, rabbit or bovine lens capsules, or in the form of lens capsule tissue pieces. The present method does not include the use of fibroblast or skin epithelial cells.

The incubation time can be determined by obtaining a second container having an interior bottom surface of about the same radius of curvature as the posterior surface of a polymethylmethacrylate optic used as a control. As in the first case, the interior bottom surface should be coated with collagen of the same type and the LEC's plated. In this case, however, the optic is removed as soon as the cells have been plated and have attached to the collagen surface, which is generally on the order of 1 day. After the optic is removed from the collagen surface, the amount of time it takes the LECs to reach approximately the center of what would have been the contact area had an optic been present is determined. This gives the approximate incubation time for step (d). In general, the immortalized LECs will grow faster than the "seeded" LECs. The incubation time for step (d) in the case of immortalized LECs will be generally on the order of 1–2 weeks, whereas in the case of LECs plated by placing pieces of lens capsule tissue on the collagen surface, it will be generally on the order of 2–3 weeks.

After the incubation in step (d), the sample is evaluated to determine whether and to what extent LECs grew on the collagen surface in the contact area. Methods for determining this amount include subjective scoring of the fraction of the contact area covered by LECs. Another method involves computer-assisted micrography image analysis. Yet another method comprises well-known dye-staining techniques. For dye-staining techniques, the sample optic would have to be removed from the contact area.

Figure 2:
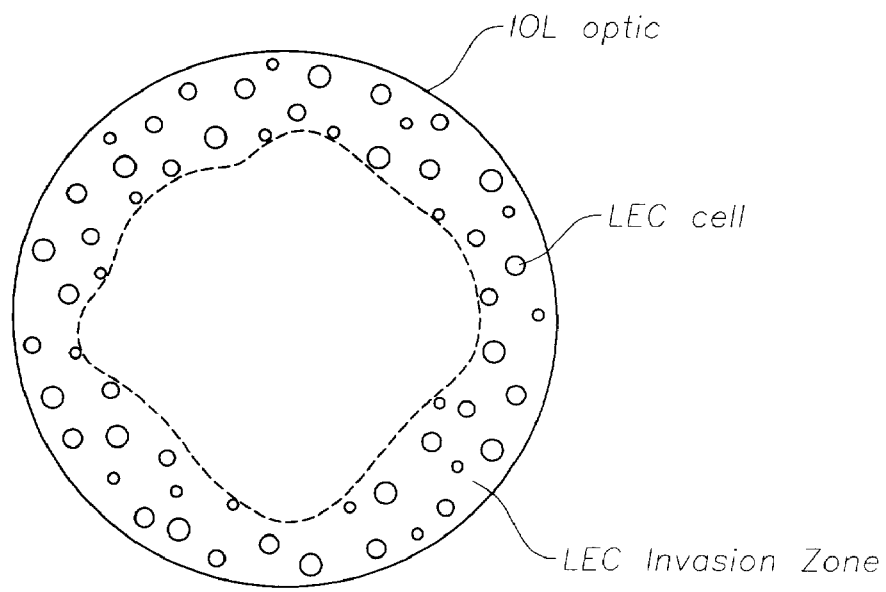
FIG. 2 shows a lens optic with an illustrated lens epithelial cell invasion zone.

As used herein, Cell Growth Index means the percentage of the surface area of the posterior side of the optic that represents the lens epithelial cell invasion zone (the area in which lens epithelial cells grew on the collagen surface in the contact area) when the optic is evaluated in the method described above. The Cell Growth Index is obtained by calculating the portion of the contact area (i.e., posterior side of the optic) covered by the lens epithelial cell invasion zone. For circular optics, the surface area of the posterior side of the optic is defined as $\Pi r^2$ (where r is the radius of the optic). The lens epithelial cell invasion zone is that portion of the contact area invaded by lens epithelial cells (see FIG. 2; the outer portion of the optic's surface area represents the lens epithelial cell invasion zone). The Cell Growth Index is 100×(surface area of lens epithelial cell invasion zone)/(surface area of the posterior side of the optic).

IOL optics having a posterior side that has a Cell Growth Index of about 33 or less are selected as IOLs having reduced or no risk of PCO. A method of preventing PCO is thus provided; the method comprises implanting into the capsular bag following extracapsular cataract extraction an IOL having a Cell Growth Index of about 33 or less.

As used herein, the Standard IOL Posterior Optic Side means an IOL posterior optic surface consisting of the copolymer formed by copolymerizing a mixture of 65 wt. % 2-phenylethyl acrylate; 30 wt. % 2-phenylethylmethacrylate; 3.2 wt. % 1,4-butanediol diacrylate; 1.8 wt. % 2-(3'-methallyl-2'-hydroxy-5'-methyl phenyl) benzotriazole, wherein the copolymer is cured using 1.8 wt. % Perkadox 16 as a polymerization initiator.

As used herein, Cell Growth Quotient of an IOL optic means the ratio of the Cell Growth Index for the IOL optic to the Cell Growth Index for an IOL optic having a posterior side consisting of the Standard IOL Posterior Optic Side. IOLs having a Cell Growth Quotient of about 1 or less are selected as particularly preferred.

The method of the present invention can be used to select IOL materials that are capable of reducing the risk of or preventing PCO. IOL materials suitable for screening using the above method can be made from any ophthalmically acceptable IOL material and include, but are not limited to, materials comprising the IOL ingredients disclosed in U.S. Pat. Nos. 5,290,892 and 5,331,073, the entire contents of which are hereby incorporated by reference.

Also preferred are IOL materials which are substantially free of glistenings in a physiologic environment and for which the amount of collagen IV that remains adhered to the material in step (d) is about 30–100% of the amount that remains adhered in step (b). Glistenings are the result of condensation of water vapor within the lens. Although glistenings have no detrimental effect on the function or performance of IOLs made from acrylic materials, it is nevertheless cosmetically desirable to minimize or eliminate them. IOL materials are substantially free of glistenings in a physiologic environment if they have an average of no more than approximately 1–2 glistenings per $mm^2$ when evaluated in the test described below. Preferably, the average number of glistenings per $mm^2$ will be much less than 1.

The presence of glistenings is measured by placement of a lens sample into a vial and adding deionized water or a balanced salt solution. The vial is then placed into a water bath preheated to 45° C. Samples are to be maintained in the bath for 24 hours. The sample is then placed either in a 37° C. bath or at room temperature and allowed to equilibrate for 2 hours. The sample is removed from the vial and placed on a microscope slide. Visualization of glistenings is done with light microscopy using a magnification of 50 to 200×.

Preferably, IOL materials are also selected so that they possess the following refractive index, $T_g$, and elongation properties, which make the materials particularly suitable for use in IOLs which are to be inserted through incisions of 5 mm or less.

The IOL material preferably has a refractive index of at least about 1.50 as measured by an Abbe' refractometer at 589 nm (Na light source). IOL optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the IOL material, which affects the material's folding and unfolding characteristics, is preferably between about −20 to +25° C., and more preferably between about −5 and +16° C. Tg is measured by differential scanning calorimetry at 10° C./min., and is determined at the midpoint of the transition of the heat flux curve.

The IOL material should also have an elongation of at least about 150%, preferably at least 200%, and most preferably about 300–600%. This property indicates that an IOL optic made of the material generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Netwon load cell. The grip distance is set at 14 mm and a crosshead speed is set at 500 mm/minute and the sample is pulled until failure. The elongation (strain) is reported as a fraction of the displacement at failure to the original grip distance.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method of determining whether lens epithelial cells will grow on the posterior capsule after an IOL optic contacts the posterior capsule, wherein the method comprises the steps of:

(a) obtaining a container having an interior bottom surface of about the same radius of curvature as the posterior side of the optic, wherein the interior bottom surface comprises a collagen surface;

(b) contacting the posterior side of the optic with the collagen surface to form a contact area, wherein the posterior side of the optic is held in contact with the collagen surface by means of a weight of about 0.5–1 g, and wherein the weight is a viewing tube having approximately the same diameter as the optic;

(c) plating lens epithelial cells on the collagen surface in an area surrounding the optic;

(d) incubating the lens epithelial cells for a time otherwise sufficient to allow the lens epithelial cells to grow to the center of the contact area; and (e) determining to what extent lens epithelial cells grew on the collagen surface in the contact area.

2. The method of claim 1 wherein in step (e) the amount of lens epithelial cells is measured using an inverted light microscope having phase contrast optics.

* * * * *